United States Patent [19]

De Lignieres

[11] Patent Number: 5,648,350
[45] Date of Patent: Jul. 15, 1997

[54] DIHYDROTESTOSTERONE FOR USE IN ANDROGENOTHERAPY

[75] Inventor: Bruno De Lignieres, Draveil, France

[73] Assignee: Laboratoires Besins Iscovesco, Paris, France

[21] Appl. No.: 676,455

[22] Filed: Jul. 8, 1996

Related U.S. Application Data

[62] Division of Ser. No. 553,302, filed as PCT/FR94/00617, May 25, 1994, abandoned.

[30] Foreign Application Priority Data

May 25, 1993 [FR] France ................................... 93 06224

[51] Int. Cl.⁶ ............................................. A61K 31/56
[52] U.S. Cl. ............................................. 514/178
[58] Field of Search ................................. 514/178

[56] References Cited

U.S. PATENT DOCUMENTS 2,927,921  3/1960  Oliveto et al. .
4,956,357  9/1990  Keenan et al. .

OTHER PUBLICATIONS

Geller, J. et al., "DHT in Prostate Cancer Tissue —A Guide to Management and Therapy", *The Prostate*, vol. 6, No. 1, 1985, pp. 19–25.

Pollard, M. et al., "Dihydrotestosterone Does Not Induce Prostate Adenocarcinoma in L–W Rats", *The Prostate*, vol. 10, No. 4, 1987, pp. 325–331.

Pollard, M. et al., "Prevention and Treatment of Experimental Prostate Cancer in Lobound–Wistar Rats. I. Effects of Estradiol, Dihydrotestosterone, and Castration", *The Prostate*, vol. 15, No. 2, 1989, pp. 95–103.

Raynaud, J. P. et al., "Cancer de la Prostate: Bases Biologiques pour l'Emploi d'un Antiandrogene dans le Traitement", *Bulletin du Cancer*, vol. 73, No. 1, 1986, pp. 36–46.

Kuhn et al., *J. Clin. Endocrinol. Metab.*, 58(2), pp. 231–235 (Biosis Abstract No. 7786041). (1984).

Kuhn et al., *Contracept. Fertil. Sex.*, 14 (11), pp. 1031–1036 (Biosis Abstract No. 83111397). (1986).

Kuhn et al., *Presse Med.*, 12, No. 1, pp. 21–25 (Derwent Abstract No. 83–13873) (1983).

Kuhn et al., *Clin. Endocrinol.*, 19, No.4, pp. 513–520 (Derwent Abstract No. 84–09329) (1983).

*Primary Examiner*—Raymond Henley, III
*Attorney, Agent, or Firm*—Young & Thompson

[57] ABSTRACT

The present invention is directed to the administration of dihydrotestosterone (DHT) for preventing prostate cancer in male patients more than 50 years old and of reducing levels of plasma-borne sex hormone binding globulins (SHBG) in male patients having elevated levels thereof.

14 Claims, No Drawings

DIHYDROTESTOSTERONE FOR USE IN ANDROGENOTHERAPY

This application is a division of application Ser. 08/553,302, filed Nov. 21, 1995, abandoned, which is A 371 of PCT/FR94/00617 filed May 25, 1994.

The present invention relates to forms of administration of dihydrotestosterone, DHT for short, whose therapeutic uses are many, and in particular the forms adapted for androgenotherapy, particularly in persons in danger of prostate hyperplasia, in particular benign hyperplasia.

It has been suggested until now that the use of DHT could result in risks for the prostate of subjects more than 50 years old. Prostate cancer and benign prostate hypertrophy, BPH for short, are disorders which depend in part on the androgens and it is easy to see that this type of risk is to be taken very seriously into consideration, particularly in the case of the treatment of andropause. From 60 years on, BPH, by comparison with the case of young adults, becomes a statistically normal condition in untreated subjects. The first period of prostate growth is connected to puberty and the testicular secretion of androgens, but hormonal influences during the second period of prostate growth after 50 years are until now far from being identified with precision.

However, experience has shown that a second rapid increase of the testicular androgen secretion is quite excluded and that on the contrary, the plasma levels of the biologically available androgens tend to decrease after 50 years. Certain authors have proposed as a plausible explanation the accumulation of DHT in the prostate tissue, but this supposition has been discarded on the basis of more recent studies comparing prostate tissues of similar origins with or without BPH.

Normal levels, even low levels, of testosterone (T for short) or of DHT, in the plasma and the prostate tissue are compatible with the development of BPH, and limited regressions of the prostate volume are described only for a substantially total suppression of the plasma testosterone in circulation or of the DHT in the prostate tissue, achieved by several pharmacological agents.

A decrease of more than 80% of the prostate tissue concentration of DHT by inhibition with 5 alpha-reductase induces only a moderate diminution of 18% of the prostate volume; and a substantial elimination of the plasma level of testosterone reduced to a mean value of 0.1 ng/ml (which is to say 50 times less than the physiological level) is necessary to induce a decrease of 30 to 40% of the prostate volume.

It will be recalled that, for example DHT has saturated nucleus A in its molecule whilst, for example, 17 beta-estradiol has a benzene nucleus A, which is to say aromatic unsaturated. The aromatic compound in question hereafter and of which testosterone is the substrate, favors the transformation of totally or partially saturated nuclei into totally unsaturated aromatic nuclei. As to alpha-reductase, inducing reduction reactions of the unsaturations permits the formation of DHT from testosterone.

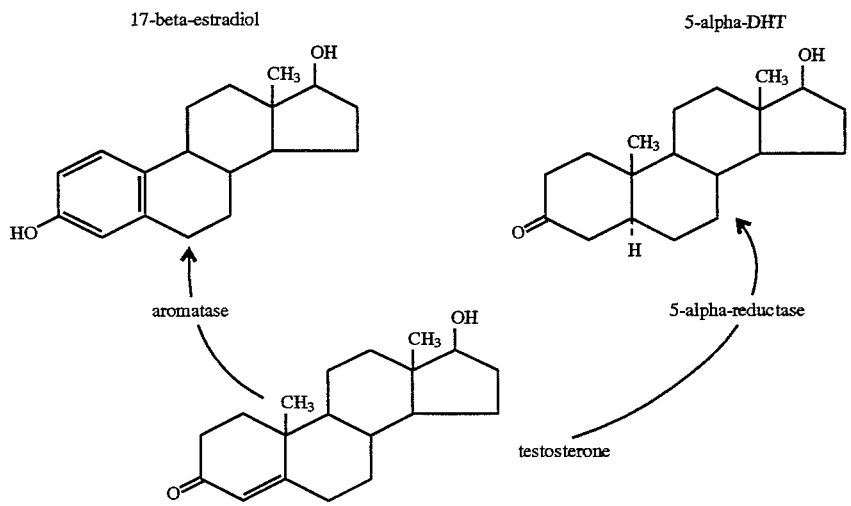

The suppositions mentioned above do not confirm the hypothesis according to which all spontaneous increase of stimulation, by T or DHT, of the epithelial or stromal prostate cells, can constitute the real initial cause of BPH in older men. They moreover do not give useful information as to the risks and rewards, for the prostate, of a moderate compensatory increase of the androgenic stimulation in older men.

As no increase, beyond physiological norms, in the stimulation by T or DHT of the prostate can explain BPH, other hypotheses have been proposed.

One of them takes into consideration the change of equilibrium, as a function of age, between estrogens and androgens. Experimental studies have shown the inability of androgens with saturated A cycles and not aromatizable as to estrogens (with totally unsaturated nucleus A) of inducing an initial condition of prostate hypertrophy. Aromatizable androgens such as testosterone or androstenedione can induce hyperplasic modifications of the prostate of monkeys, but these effects are reversed by addition of an aromatase inhibitor.

Similarly, 14 months of treatment with non-aromatizable DHT, of male Lobund-Wistar (LW) rats susceptible to prostate cancer, have not induced either macroscopic or microscopic hypertrophy, nor prostate cancer. Conversely, rats treated with equivalent doses of testosterone have shown an increased incidence of benign hypertrophy, and an adenocarcinome has been detected in 24% of the animals treated, with additional in situ tumors in 16%. Among the untreated reference group, there has been observed an intermediate situation for several cases of BPH and several in situ neoplasms, but without encroaching adenocarcinome.

Such experiments lead one to believe that, in animals with a high risk of prostate disorder, T and DHT have very different influences, a long treatment by aromatizable testosterone increasing the incidence, both of malignant and of benign prostate disorders, whilst treatment with non-aromatizable DHT decreases these two risks. A short-term study with an aromatase inhibitor in men suffering from BPH has shown a mean reduction of 26% of the prostate volume, which reinforces the hypothesis of the responsibility, also for men, of certain estrogens.

All this leads to the thought that there exists an effect of estrogens on the prostate. It has been possible to identify estradiol receptors in the normal human prostate or in an initial condition of BPH for higher concentrations in the stromal cells than in the epithelial cells.

There has been identified the activity of aromarase for locally synthesizing estrogens from substrates such as testosterone or androstane-dione, in the stromal portion of the prostate.

Moderate concentrations of estrogens in the presence of androgens stimulate specifically the short-term stromal increase, but for the medium and long term, the stromal cells influence the epithelial increase by pancreatic effects, whilst the androgens, in particular DHT, influence particularly the epithelial increase and maintain a physiological equilibrium between stroma and epithelium.

Not only does the activity of aromarase tend to increase with age, but experience suggests a slight tendency toward less sensitivity of the prostate cells to DHT with age, and on the contrary, toward a greater sensitivity to estradiol.

Stimulation with estradiol can relatively increase as a function of the increase of the plasma level of the estrogens, of the aromatization of the testosterone of the tissues and of the potential receptivity of the stromal cells due to autocrine/paracrine changes.

In the first instance, the stroma proliferate, creating growing nodules which influence, in a second stage, the glandular elements by pancreatic stimulation. In a third stage, the autocrine/panacrine factors will maintain the stromal and epithelial cells under control, the more rapidly increasing portion of the tissue becoming independent of any steroidal stimulation.

One can thus conclude that neither DHT alone, nor estradiol alone, can overstimulate the stromal or epithelial prostatic cells. In middle-aged men, the modifications of the prostate appear to result from a progressive increase of the estradiol/DHT ratio in the stroma.

In the prior art, most of the hormonal treatments are directed toward suppression of androgens and have given rise to objective improvement only when the androgen stimulation has been reduced to a level nearly zero. Such a situation does not respond to the needs of an andropause hormonal substitution.

Moreover, an anti-androgenic treatment can more suppress the normal cells depending on the androgens than the cells stimulated by the estrogens, which is potentially harmful in the long run; this advantage could be limited as to time.

Moreover, a treatment with DHT, which, contrary to that with testosterone, includes both an androgenic and an anti-aromatizing activity, is fairly attractive for its theoretical aptitude possibly to increase the androgenic stimulation whilst preventing or considerably reducing the tendency, with age, toward increase of the estradiol/DHT ratio. The decrease of the estrogens, contrary to that of the androgens, does not have an appreciable secondary effect in older men.

According to a third hypothesis, it is considered that the marked increase with age of the sex hormone binding globulins (SHBG for short) constitutes the best pathogenic explanation for prostate disorders.

This type of globulin constitutes the vehicle for the sex hormones. An excess of SHBG not bound to steroids, is adapted to bind to certain receivers of the prostate cellular membranes, and to trigger stimulating effects on the cellular growth.

The growth in vitro, of human carcinomal cells, is stimulated by the addition of SHBG to the culture medium. A supplemental addition of testosterone does not modify or reinforce the effect of the SHBG.

Conversely, the addition of DHT in high concentration reduces this stimulation effect. The saturation of the sites with a high affinity for plasmic SHBG, with DHT, prevents the binding of the SHBG to the receptors of the cellular membranes.

This last hypothesis is compatible with the preceding one, because the increase of SHBG seems to be connected to an increase as a function of age in the activity of aromatase in the liver, and moreover this suggests also a potential advantage. in the use of DHT relative to testosterone.

Finally, the instability of the androgenic stimulation can mask the pathogenic importance, because an intermittent androgenic stimulation of the prostate stimulates experimentally more mitose in the epithelium of the prostate than a constant and stable concentration of androgens.

It might be supposed according to these previous studies, that compositions of testosterone with prolonged action, with large variations of the plasmatic androgens, are less than optimum for in vivo studies of the human prostate.

To summarize, it can be said that there has been proposed essentially in the prior art:

a) decreasing the level of activity of the 5 alpha-reductase in the prostate resulting in a decrease of the DHT level, b) using an antiaromatase and producing a drop in estrogen concentrations.

The drawbacks of these methods have been emphasized which do not permit in any case reestablishment of physiological androgenic stimulation.

The administration of DHT in the form of a percutaneous gel or an injectable heptanoate by intramuscular path. has not been envisaged in the prior art other than for the treatment of gynecomasty or hypogonadism. But it is evident. that the benefits and the risks, in particular prostatic, in adolescents and young adults are different from those in older men or, more generally, those over 50 years. This type of administration is described in European patent application 0 197 753 with priority of Mar. 30, 1984 filed in the name of Baylot College of Medicine.

According to the present invention, resort is had to the antiaromatization effect connected with the increase of DHT level. But whilst the prior art considered that DHT was harmful as to prostate hypertrophy, the invention is based on the use of higher plasmatic concentrations evident upon fixed dosages, which give the reverse effect of that expected until now. This effect which is contrary to usual considerations had never been described and is effective, as will be seen later on.

Moreover, according to a preferred embodiment of the invention, the compositions are administered by percutaneous route and hence the active principles are distributed in a more regular and prolonged fashion timewise, than in the case of injections which give rise to large variations in the active principle among individuals, as in the case of the European application cited above.

Those skilled in the art should administer quanties of DHT which assure a plasmatic content of the order of 2.5 to 10 ng/ml. The doses administered will therefore depend on the initial level in the patient and the desired level. Blood analyses permit following the progress and varying the administered doses as a result.

It will also be noted that the sum of the plasmatic contents of T+DHT is on the average higher than 3.5 ng/ml in normal humans. The testosterone level, on the average, is ten times greater than that of DHT. According to the invention, this ratio is reduced and even reversed, and according to the invention the preferred goal will be more than 3 ng/ml of DHT for less than 1.5 ng/ml of testosterone.

In order better to understand the technical characteristics and advantages of the present invention, there will now be described an example of embodiment, it being of course understood that this is not limitative as to its mode of use and as to the uses that can be made of it.

The following composition is used, constituted by a hydroalcoholic gel with a DHT content of 0.5 to 3.5%, preferably 2.5%.

5 to 10 g of this gel are administered per day percutaneously, as needed, applied over a large surface (arms, forearms, shoulders). The plasma level of T and DHT is monitored, and the daily dose is corrected as a consequence to maintain these levels within the above limits.

Comparative tests have been carried out as follows:

In the course of studies carried out by the applicant, the prostate evolution has been followed in 37 men aged 55 to 70, with high plasma levels of SHBG and clinical symptoms attributed to hypergonadism, and this with a treatment with DHT by percutaneous route and for a duration of 6 months to 5 years.

In 27 subjects in which the plasma DHT level was controlled, so as to modulate the administered doses, said levels have been increased to 2.5 to 6 ng/ml. There resulted a decrease in gonadotrophy as well as in the plasma levels of testosterone which exceeded at least 1.5 ng/ml (from 0.5 to 1.4 according to the case); as to the estradiol plasma levels, these decreased by 50%.

Among this group of subjects, the volume of the prostate diminished significantly, as was evaluated by ultrasound and by PSA (Prostate Specific Antigen). The mean volume of the prostates was from 31.09±16.31 grams before treatment and from 26.34±12.72 grams after treatment, for a mean reduction of 15.4%, the treatment having a mean duration of 1.8 years with DHT (P=0.01).

By contrast, in a group of 10 men with lower plasma levels of DHT, which is to say less than 2.5 ng/ml, that were treated with the same compositions without regard to the variations in plasma level and hence without modulation of the administered doses, there was Been less diminishing of the plasma levels of testosterone, which remained above 2 ng/ml, and no variation of the estradiol plasma levels, with a slight and insignificant increase in the volume of the prostate which changed from 31.6±16.38 grams before treatment to 36.15±16.62 grams after treatment of a mean duration of 1.7 years, namely +14.4% increase.

I claim:

1. A method for prevention of hyperplasia of the prostate, comprising administering to male patients more than 50 years old, an amount of dihydrotestosterone (DHT) effective to increase a plasmatic content of DHT to a value from about 2.5 to about 10 ng/ml.

2. The method according to claim 1, wherein said amount is effective to increase the sum of the plasmatic contents of testosterone (T) and DHT to a value higher than 3.5 ng/ml.

3. The method according to claim 2, wherein said DHT is administered percutaneously.

4. The method according to claim 3, wherein said DHT is administered in the form of a composition having a DHT content of 0.5 to 3.5%.

5. The method according to claim 4, wherein said DHT content is about 2.5%.

6. The method according to claim 4, wherein said composition is a hydroalcoholic gel.

7. The method according to claim 6, wherein said effective amount is 5–10 g of said gel per day.

8. A method of reducing levels of plasma-borne sex hormone binding globulins (SHBG), comprising administering to male patients having elevated levels of plasmic SHBG, an amount effective to increase a plasmatic content of DHT to a value from about 2.5 to about 10 ng/ml.

9. The method according to claim 8, wherein said amount is effective to increase the sum of the plasmatic contents of testosterone (T) and DHT to a value higher than 3.5 ng/ml.

10. The method according to claim 9, wherein said DHT is administered percutaneously.

11. The method according to claim 10, wherein said DHT is administered in the form of a composition having a DHT content of 0.5 to 3.5%.

12. The method according to claim 11, wherein said DHT content is about 2.5%.

13. The method according to claim 11, wherein said composition is a hydroalcoholic gel.

14. The method according to claim 13, wherein said effective amount is 5–10 g of said gel per day.

* * * * *